United States Patent [19]

Huau

[11] Patent Number: 4,970,695
[45] Date of Patent: Nov. 13, 1990

[54] IN SITU CALIBRATION OF A SENSOR

[75] Inventor: Christian Huau, Fonenay-aux-Roses, France

[73] Assignee: Schlumberger Technology Corporation, New York, N.Y.

[21] Appl. No.: 494,721

[22] Filed: Mar. 16, 1990

[30] Foreign Application Priority Data

Mar. 17, 1989 [FR] France ................. 89 03535

[51] Int. Cl.$^5$ ................. G01V 1/00; H04B 17/00
[52] U.S. Cl. ................. 367/13; 367/35; 181/105
[58] Field of Search ............ 367/13, 902, 35; 181/105; 73/1 DV

[56] References Cited

U.S. PATENT DOCUMENTS

| | | | |
|---|---|---|---|
| 2,631,270 | 3/1953 | Goble | 367/104 |
| 4,524,433 | 6/1985 | Broding | 367/35 |
| 4,685,092 | 8/1987 | Dumont | 367/35 |

FOREIGN PATENT DOCUMENTS 0176408 9/1985 European Pat. Off. .
2094473 3/1982 United Kingdom .

Primary Examiner—Thomas H. Tarcza
Assistant Examiner—Daniel T. Pihulic
Attorney, Agent, or Firm—Clifford L. Tager

[57] ABSTRACT

Logging equipment for use in a borehole has a sensor such as an ultrasonic sensor, oriented radially towards the wall of the borehole and rotatable in one direction during measurement about the longitudinal axis of the equipment. In order to allow the sensor to be recalibrated downhole, the equipment also includes a target which is automatically brought face to face with the sensor upon reversal of the direction of rotation of the sensor. The sensor can thus be calibrated under conditions which are as close as possible to the conditions of measurement.

7 Claims, 5 Drawing Sheets

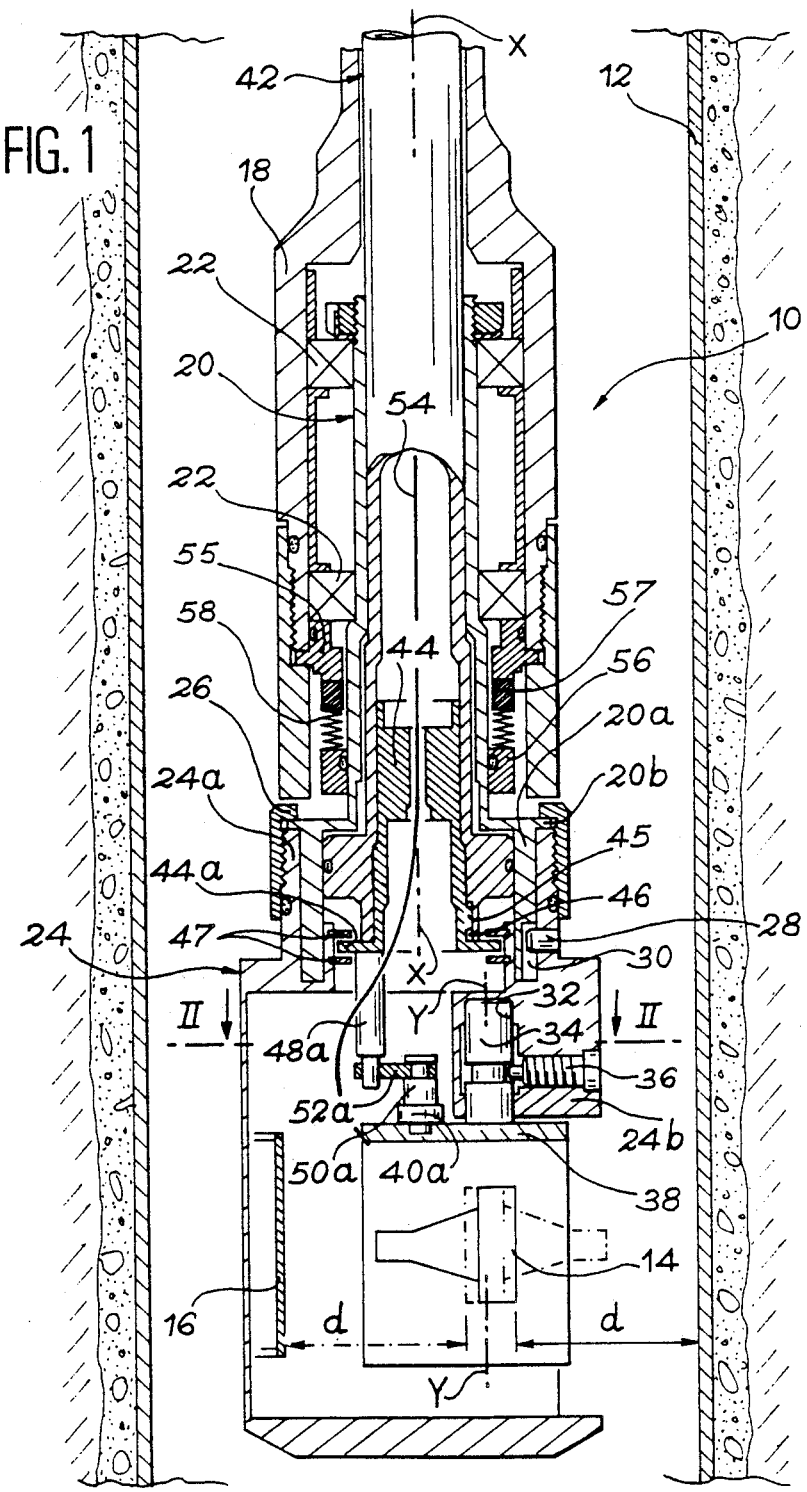

IN SITU CALIBRATION OF A SENSOR

BACKGROUND OF THE INVENTION

1. Technical Field

The present invention is directed to using a rotating sensor to scan the wall of the borehole. More particularly, the present invention is directed to using a rotating sensor, e.g., sonic or ultrasonic, to circumferentially scan the borehole wall.

2. Background Information

In order to perform measurements, e.g., to evaluate the quality of the cement bond with the casing of the well, various types of measurement apparatus have been developed.

For example, U.S. Pat. No. 4,524,433 to Broding, herein incorporated by reference, discloses an apparatus having at least one measurement sensor which points radially relative to the longitudinal axis of the apparatus and rotates to circumferentially scan the wall of the borehole. By combining this rotary motion of the sensor with the translation motion of the apparatus along the borehole, the wall of the borehole is scanned along a helical trajectory.

In measurement apparatus designed in this manner, there is no way of recalibrating the measurement sensor in situ as it scans the borehole. The operating conditions of the apparatus, e.g., temperature and pressure, vary along the borehole, and frequenttly result in changes in the measurements performed. In the absence of recalibration, this can lead to significant errors.

U.S. Pat. No. 4,685,092 to Dumont, herein incorporated by reference, describes a measurement apparatus wherein a plurality of fixed measurement sensors are directed radially towards the wall of the borehole. These measurement sensors are placed on the apparatus along a helix such that displacing the apparatus parallel to its own axis inside the borehole has the effect of scanning the major portion of the wall of the borehole.

Compared with Broding, Dumont does not provide a complete azimuth coverage of the wall of the borehole. Dumont does, however, teach a calibration means comprising a calibration sensor which is distinct from the measurement sensors and which points downwards, along the longitudinal axis of the apparatus, towards a calibrating target facing this sensor.

By providing substantially the same distance between the target and the calibration sensor as occurs between the measurement sensors and the wall of the borehole, the sensor can be periodically recalibrated while the borehole is being scanned.

However, this solution is only partially satisfactory, in particular due to the fact that the calibration sensor is distinct from the measurement sensors. As a result, the calibration does not take account of any dispersion phenomena that may exist between the measurement sensors. In addition, the calibration sensor points in a different direction than the measurement sensors so that the motion of the fluid contained in the borehole relative to the calibration sensor is not representative of the motion of the same fluid relative to the measurement sensors.

SUMMARY OF THE INVENTION

The object of the present invention is to provide a logging method and apparatus in which a target can be placed in front of a sensor pointing towards the wall of the borehole, in order to allow calibration of the sensor under conditions which are close to those which prevail during measurement.

According to the invention, this result is obtained by a logging method comprising a measurement step in which a sensor is caused to rotate in one direction in order to scan the wall of the borehole circumferentially, and a calibration step in which the sensor and a target are brought face to face by reversing the direction of rotation of the sensor, whereby a reference measurement for calibrating the sensor can be obtained.

Preferably, the distance between the sensor and the target during the calibration step is substantially equal to the distance between the sensor and the wall of the borehole during the measurement step. In addition, with the rotation of the sensor being performed about an axis substantially parallel to the longitudinal axis of the borehole during the measurement step, the sensor and the target are preferably brought face to face substantially perpendicularly to the longitudinal direction during the calibration step.

Advantageously, a target is used having limited angular lost motion relative to the sensor such that during a measurement step, the rotation of the sensor in said one direction is imparted to the target occupying a first angular position offset relative to the sensor, and when the direction of rotation of the sensor is reversed, this rotary motion is imparted to the target occupying a second angular position facing the sensor after said angular lost motion has been taken up.

The invention also provides a logging apparatus adapted for use in a borehole, the apparatus comprising a housing, a sensor rotatable about a longitudinal axis of the housing, and drive means for rotating the sensor about said axis in one direction to scan the wall of the borehole, the apparatus further comprising a target and displacement means responsive to the direction of rotation of the sensor for displacing the sensor and the target relative to each other from a measurement position in which the sensor is oriented towards the wall of the borehole to a calibration position in which the sensor faces the target when the direction of rotation is reversed.

Advantageously, the displacement means comprise motion transmission means defining limited angular lost motion such that when the sensor is rotated in said one direction the target occupies a measurement position which is angularly offset relative to the sensor and when the sensor is rotated in the opposite direction, the target occupies the calibration position.

Preferably, the apparatus includes a rotary head carrying a target support and rotatable about the longitudinal axis of the casing, and the sensor is rotatably supported by the target support about a first axis which is parallel to and offset from the longitudinal axis of the housing.

In order to allow adaptation of the apparatus to the dimensions of the borehole, it is advantageous to provide an interchangeable target support on the rotary head.

In addition, the sensor is preferably removably fixed on a sensor support which is itself rotatable on the target support, whereby the same sensor can be used with different target supports.

In a first preferred embodiment of the invention, suitable for use with small-sized sensors, the target support is fixed on the rotary head and the motion transmission means defining said limited angular lost motion are placed between the sensor and the target support. The rotary drive means for the sensor then comprise a drive shaft mounted on said longitudinal axis inside the rotary head and a mechanism for transmitting the rotary motion of the shaft to the sensor.

In a second preferred embodiment of the invention suitable for use with sensors which are larger in size, the target support is supported by the rotary head about a second axis parallel to and offset from the first axis and the longitudinal axis of the casing, said second axis being situated between the first axis and the longitudinal axis when the sensor rotates in the measurement direction and the means for transmitting motion and defining the limited lost motion are placed between the rotary head and the target support.

In this case, the means for rotating the sensor comprise the rotary head and a mechanism for transmitting rotary motion from the head to the sensor.

BRIEF DESCRIPTION OF THE DRAWINGS

FIG. 1 is a longitudinal section view showing the bottom end of measurement equipment located in a borehole and including apparatus in accordance with a first embodiment of the invention.

DESCRIPTION OF THE PREFERRED EMBODIMENT

In FIG. 1, reference 10 designates the bottom end of measurement equipment intended, for example, to inspect the cementing of casing 12 in a borehole which is nominally cylindrical, such as a borehole for hydrocarbon production.

Measurement equipment 10 includes sensor 14 such as an ultrasonic sensor which is normally directed radially towards the wall of the well i.e. towards the casing 12, relative to the longitudinal axis XX of the equipment, thereby performing measurement at a distance.

Figure 2A:
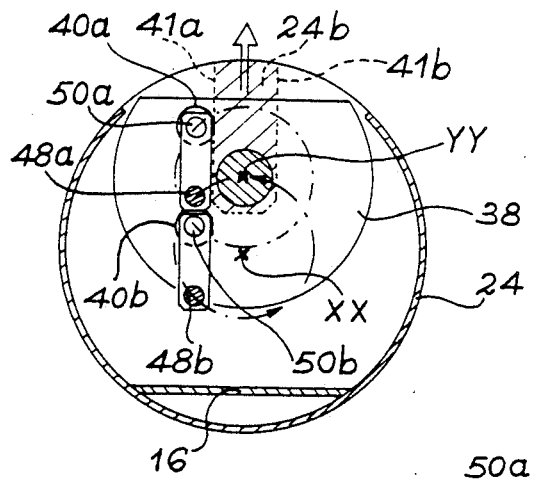
FIGS. 2A to 2D are section views on line II—II of FIG. 1 showing various relative angular positions of the sensor and the target support in the equipment.

Means described in greater detail below for rotating the sensor 14 about the longitudinal axis XX of the equipment enable the wall of the borehole to be scanned completely in azimuth when rotation is caused to take place clockwise as shown in FIG. 2A. Simultaneously, the equipment is preferably raised at a constant translation speed along its longitudinal axis by conventional means (not shown) situated above the ground. This causes the sensor to scan the wall of the borehole helically.

In order to ensure that the distance between sensor 14 and the wall remains practically constant throughout this scanning motion, the measurement equipment is fitted in conventional manner with centering means constituted, for example, by extensible arms (not shown) brought into contact with the wall of the borehole. Longitudinal axis XX of the equipment then coincides substantially with the axis of the borehole.

According to the present invention, in order to calibrate sensor 14 inside the borehole, the measurement equipment also includes calibrating target 16 disposed parallel to longitudinal axis XX of the equipment and situated at the same level as the sensor. Target 16 and sensor 14 are mounted on the equipment in such a manner that a reversal of the direction of rotation of the sensor about the longitudinal axis of the equipment brings the target automatically in front of the sensor under conditions which are close as possible to the conditions under which in situ measurements are performed by the sensor.

To this end, the target has characteristics which are as close as possible to those of casing 12 under inspection. The distance between the sensor and the target in the calibration position is as close as possible to the distance between the sensor and the casing during measurement. The fluids present in the borehole also have relatively comparable flow characteristics in both positions.

In the embodiment shown in FIGS. 1 to 3, sensor 14 is sufficiently small for the above-specified conditions to be obtained merely by rotating the sensor about an axis YY parallel to, and offset from, longitudinal axis XX of the equipment.

As shown in greater detail in FIG. 1, this result is obtained in practice by means of measurement equipment 10 including non-rotating tubular outer housing 18 in which hollow outer shaft 20 is rotatably mounted by means of two bearings 22. This hollow outer shaft 20 constitutes a rotary head which extends downwards beyond the bottom end of the housing 18 in order to support target support 24 on which target 16 is fixed.

More precisely, target support 24 is removably fixed on tubular bottom portion 20a of hollow shaft 20, e.g., by means of ring 26 screwed on a threaded tubular top portion 24a of support 24 so as to clamp flange 20b fixed to shaft 20 against the top edge of threaded tubular portion 24a. Stud 28, mounted in threaded top end 24a of support 24, projects radially inwardly into longitudinal groove 30 formed in tubular bottom portion 20a of shaft 20 so as to prevent relative rotation occurring between the shaft and support 24.

Thus, the assembly constituted by outer hollow shaft 20 and target support 24 is free to rotate relative to outer housing 18 of the equipment about longitudinal axis XX thereof. Regardless of the angular position of this assembly, target 16 is fixed on support 24 in such a manner as to be permanently disposed parallel to longitudinal axis XX of the equipment and to be situated at a constant distance from said axis.

At a location diametrically opposite target 16 about longitudinal axis XX of the equipment, target support 24 includes block 24b adjacent to threaded tubular portion 24a and in which bore 32 is formed about axis YY. Cylindrical rod 34 is mounted to rotate in bore 32 and is restrained from translation by screw 26 engaged in block 24b and having an end received in a groove in cylindrical rod 34.

The bottom end of cylindrical rod 34 is fixed to support plate 38 extending radially relative to axis XX and YY and constituting the support for sensor 14. Sensor 14 is removably fixed on support plate 38 by fixing means such as screws (not shown).

It should be observed that distance d between sensor 14 and the inside wall of the borehole when the sensor is directed radially towards said borehole relative to axis XX is approximately equal to the distance between the same sensor and target 16 when the sensor is rotated through 180° about axis YY, as shown in FIG. 1 by dot-dashed lines.

While measurement is being performed, sensor 14 must be permanently directed towards the wall of the borehole, and distance d between the sensor and the wall should remain constant. Rotary drive for the sensor must therefore be transmitted to entire target support 24 so that the sensor does not rotate about axis YY and so that the sensor rotates in unison with support 24 about axis XX.

In addition, the means for transmitting the rotary motion of sensor 14 in the measurement direction to target support 24 define angular lost motion such that when the direction of rotation of the sensor is reversed, the sensor is free to rotate about axis YY through an angle close to 180° so as to come face to face target 16. When such rotation of sensor 14 in the opposite direction continues beyond 180°, the rotation is again transmitted to support 24 carrying target 16 such that sensor 14 remains face to face with the target. The sensor can be recalibrated or an analogous operation can then be performed under conditions which are substantially identical to measurement conditions, both with respect to the sensor-target distance and with respect to the direction and speed of the flow of the fluid present in the borehole between the sensor and the target.

Figure 2B:
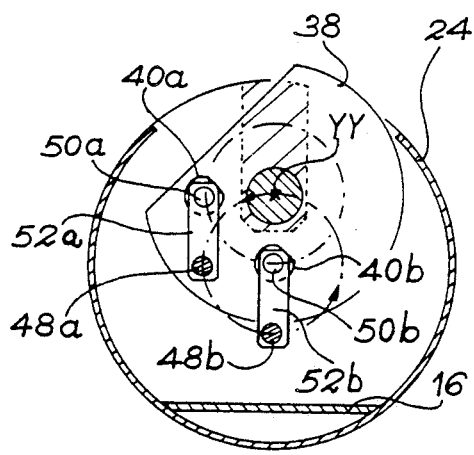
Figure 2C:
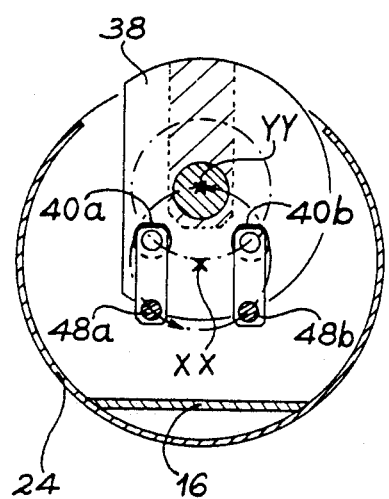
Figure 2D:
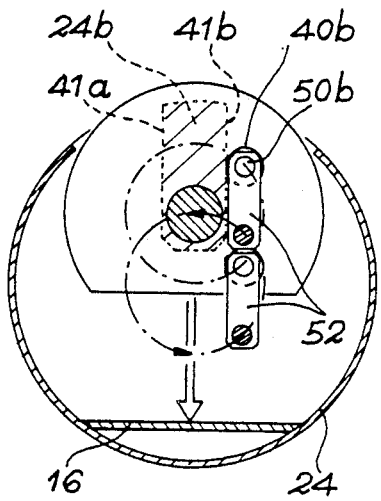

In practice, in the embodiment in FIG. 1 and FIGS. 2A to 2D, the means for transmitting the rotary motion of the sensor to the target with angular lost motion limited to about 180° comprise two abutments, 40a and 40b, which project from support plate 38 from the same side as cylindrical rod 34, thereby being suitable for coming into abutment against opposite faces 41a and 41b of block 24b. The two extreme positions correspond respectively to abutment 40a bearing against face 41a of the block, and to abutment 40b bearing against face 41b, and these positions are shown in FIGS. 2A and 2D, respectively. They are separated by counterclockwise rotation of sensor support plate 38 about axis YY relative to target support 24 and through about 180°.

The measurement equipment shown in FIG. 1 also includes means for rotating sensor 14 either in a first direction, for performing the desired measurement of the inside of the borehole, or in the opposite direction, to recalibrate the sensor.

These drive means comprise inner hollow shaft 42 which is mounted to rotate inside outer hollow shaft 20. Shaft 42 has its top end connected to a motor for imparting rotary drive (not shown) and associated with means for reversing the direction of rotation of the shaft. Cylindrical drive part 44 is received in the bottom end of hollow shaft 42. This drive part includes key 45 on its outside surface which is received in axial groove 46 formed inside shaft 42. Drive part 44 is thus constrained to rotate together with shaft 42 while still being capable of being separated therefrom by being moved downwards, as described below.

The bottom end of drive part 44 includes flange 44a which is retained with a small amount of axial clearance between two washers 47 mounted in two circumferential grooves inside tubular top portion 24a of target support 24. This structure makes it possible normally to prevent part 44 from moving in translation relative to hollow drive shaft 42, while allowing part 44 to be removed together with target support 24 when ring 26 is unscrewed.

The bottom face of flange 44 carries two cylindrical rods 48a and 48b which are oriented parallel to axis XX and which are disposed at equal distances therefrom. The top face of support plate 38 also carries two cylindrical rods 50a and 50b oriented parallel to axis YY and equidistant therefrom. The distance between axes 48a and 48b is preferably the same as the distance between axes 50a and 50b, as can be seen in FIGS. 2A to 2D.

Two parallel links 52a and 52b lying in a plane extending radially relative to axes XX and YY are hinged at their ends to the ends of cylindrical rods 48a and 50a, and 48b and 50b, respectively. The system constituted in this way forms a deformable parallelogram having two of its sides constituted by links 52a and 52b for identically transmitting any rotation of drive shaft 42 and of part 44 to support plate 38 of sensor 14.

Advantageously, although it is not critical, abutments 40a and 40b are formed by larger diameter portions formed at the bases of cylindrical rods 50a and 50b, as shown in FIGS. 1 and 2.

By virtue of the above-described arrangement, when drive 42 rotates clockwise (as shown in FIG. 2A), abutment 40a normally bears against side face 41a of block 24b of support 24, such that sensor 14 cannot rotate about axis YY and the assembly constituted by sensor 14 and support 24 for target 16 rotates in unison about axis XX. Sensor 14 is then oriented radially towards the wall of the borehole. By causing equipment 10 to move upwards simultaneously in translation parallel to axis XX, the sensor is caused to perform helimotion, thereby enabling measurements to be performed.

When, at any moment either before measurement, or after measurement, or during measurement, it is desired to calibrate sensor 14, it suffices, in accordance with the invention, to reverse the direction of rotation of drive shaft 42.

As shown in FIGS. 2B and 2C, drive shaft 20 rotates two cylindrical rods 48a and 48b counterclockwise about axis XX. This rotary motion is transmitted, as before, to plate 38 supporting sensor 14 by means of links 52a and 52b and via cylindrical rods 50a and 50b. However, given that the direction of rotation has been reversed, abutment 40a which was pressed against face 41a of block 24b moves away from this block such that rotation of plate 38 is not transmitted to target support 24. Consequently, under the effect of inertia and friction, relative rotation occurs between plate 38 supporting sensor 14 and support 24 carrying target 16, about axis YY and as shown successively in FIGS. 2B and 2C.

As shown in FIG. 2D, this rotation of sensor 14 about axis YY continues until second abutment 40b abuts against face 41b of block 24b. Advantageously, this abutting engagement occurs when sensor 14 has rotated through 180° about axis YY, such that it is then face to face with target 16.

The sensor car then be recalibrated under conditions which are as close as possible to measurement conditions, since the distance between the sensor and the target is approximately equal to the distance between the sensor and the wall of the borehole during measurement and since the flow of the fluid contained in the borehole between the sensor and the target is a flow which occurs at practically the same speed and in the same direction as the flow of the fluid between the sensor and the wall during measurement. Calibration preferably takes place while the assembly constituted by the sensor and the target is rotating in unison about axis XX of the equipment at the same speed as it rotates during measurement, but in the opposite direction, and only translation of the equipment parallel to axis XX is generally stopped. Given that calibration takes place in situ, environmental conditions such as temperature and pressure are obviously the same as those which prevail during measurement.

For the preferred embodiment, electrical conductors 54 are placed inside inner drive shaft 42 and pass through part 44 in order to have one end connected to plate 38 supporting sensor 14. The top ends of electrical conductors 54 are connected to a conventional electrical module of the equipment (not shown) serving simultaneously to provide the sensor with the electrical signals it requires to operate and also to perform preliminary processing of the signals provided by the sensor.

Electrical conductors 54 rotate together with shaft 42 and part 44, and they include (at the top portion of part 44) a connector suitable for allowing support 24 carrying both target 16 and sensor 14 to be removed (connector not shown). Electrical connection between the ends of electrical conductors 54 connected to plate 38 and sensor 14 is provided by contacts which are automatically connected electrically when sensor 14 is fixed on support plate 38, while nevertheless allowing the sensor to be removed therefrom.

In a manner which is conventional for equipment used in boreholes, measuring equipment 10 also includes means for sealing from the borehole medium the portion of the equipment situated inside housing 18 above part 44. These means comprise, in particular, two end rings 55 and 56, respectively, connected in sealed manner on housing 18 and on outer hollow shaft 20, and ring 57 connected to ring 55 by expandable bellows 58 and slidable on ring 55.

Figure 3A:
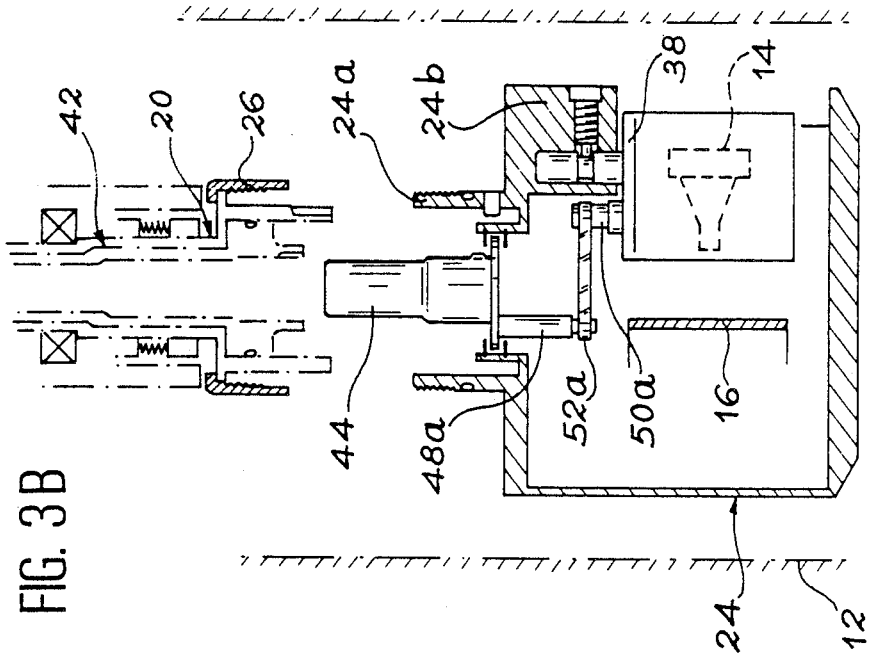
FIGS. 3A and 3B are diagrammatical longitudinal section views comparable to FIG. 1, showing how the equipment can be adapted to boreholes of different diameters by virtue of the target support being interchangeable.
Figure 3B:
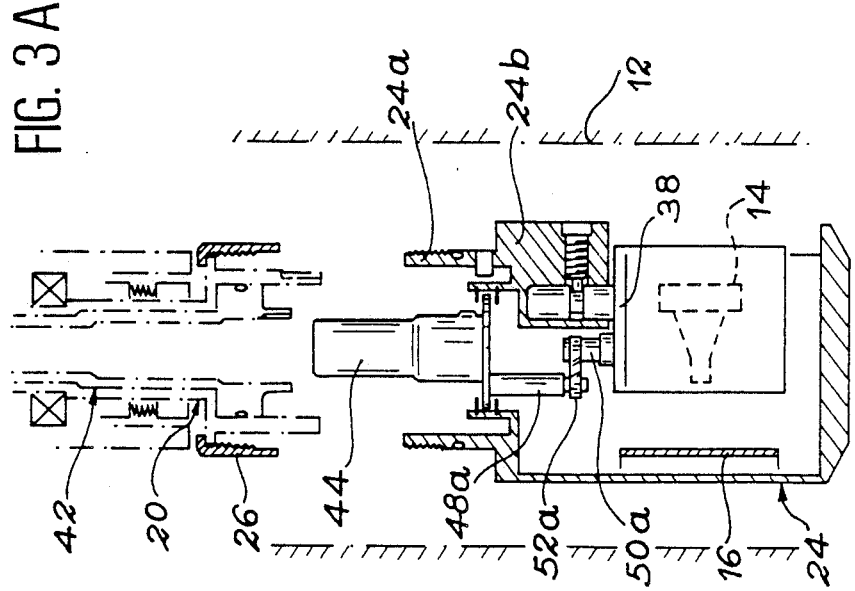

FIGS. 3A and 3B show that the bottom portion of measurement equipment 10 described with reference to FIG. 1 is interchangeable, and thus the same equipment can be used for performing measurements in boreholes of different diameters.

Thus, FIGS. 3A and 3B show that the assembly constituted by target support 24, drive part 44, target 16 fixed on support 24, plate 38 supporting sensor 14, and the mechanism for transmitting rotary motion of part 44 to plate 38 and including, in particular, links 52a and 52b, constitutes an interchangable module. This module is removed merely by unscrewing ring 26.

Each module is a different size suitable for performing measurements in boreholes of different diameters. More precisely, target support 24 defines the distance between longitudinal axis XX of the equipment and axis of rotation YY of the sensor. Given that the dimensions of sensor 14 are, in practice, always the same, this distance increases with increasing borehole diameter so as to ensure that the distance d between the sensor and the facing wall of the borehole while measurements are being performed always lies within given limits which depend on the characteristics of the sensor and regardless of the diameter of the borehole.

In each module, drive part 44 and plate 38 supporting sensor 14 are all identical, such that changes in the distance separating axes XX and YY give rise merely to changes in the length, and optionally the shape, of links 52.

Further, in order to ensure that the distance between sensor 14 and target 16 in the sensor-calibrating position always lies within said determined limits, so that said distance is approximately equal to the distance between the sensor and the wall of the borehole in the measurement position, target 16 is mounted in support 24 in such a manner that the distance between said target and axis YY is always practically the same, as shown in FIGS. 3A and 3B.

It should be observed that support 24 forms a closed cage beneath the sensor and the target, and behind the target it includes a portion in the form of a section of an arc of a circle centered on axis XX and whose distance from the wall of the borehole is approximately constant, regardless of the diameter of the borehole.

Finally, in order to ensure that the equipment is centered inside the borehole without too much difficulty, the various parts constituting the equipment, and in particular the rotary portion thereof, are designed to keep the assembly balanced as well as possible on a permanent basis about axis XX of the equipment.

In the embodiment described above with reference to FIGS. 1 to 3, sensor 14 is small enough to enable it to be brought face to face with target 16 merely by being rotated about axis YY and without any interference occurring between the sensor and the wall of the borehole. However, when a larger sensor is used, it may be necessary to combine this rotary motion of the sensor about its axis with an additional motion for recentering the assembly formed by the sensor and the target relative to axis XX of the equipment.

Figure 4B:
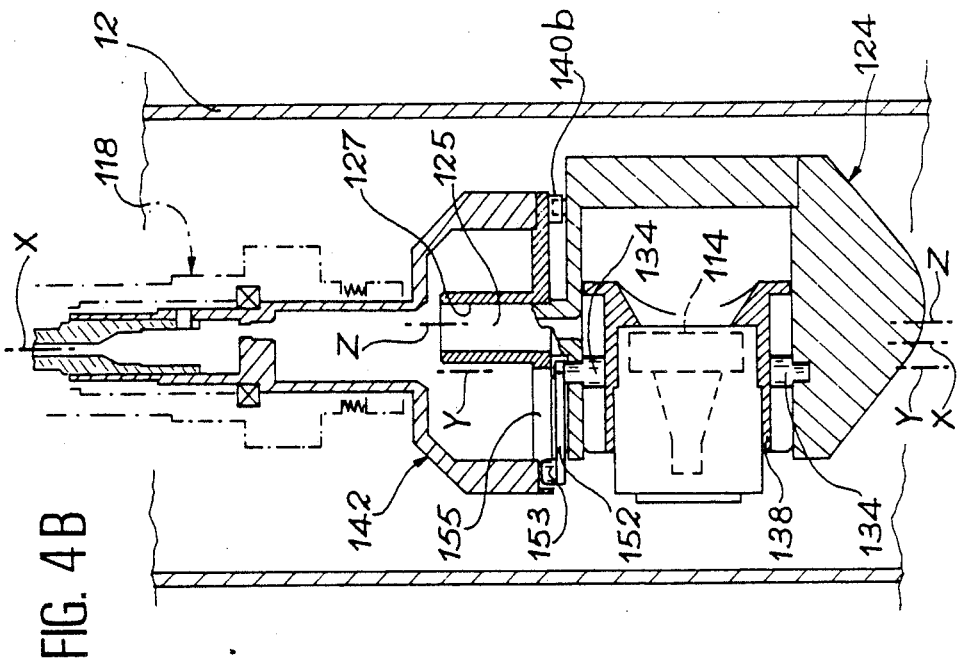
FIGS. 4A and 4B are longitudinal section views through measurement equipment including apparatus in accordance with a second embodiment of the invention, with the various parts of the apparatus being shown respectively in the positions they occupy during measurement and during calibration.

A second embodiment of the invention putting this idea into effect is described with reference to FIGS. 4 and 5.

In the embodiment shown with reference to FIGS. 4 and 5, the same reference numerals plus 100 are used for designating items having analogous functions.

Figure 4A:
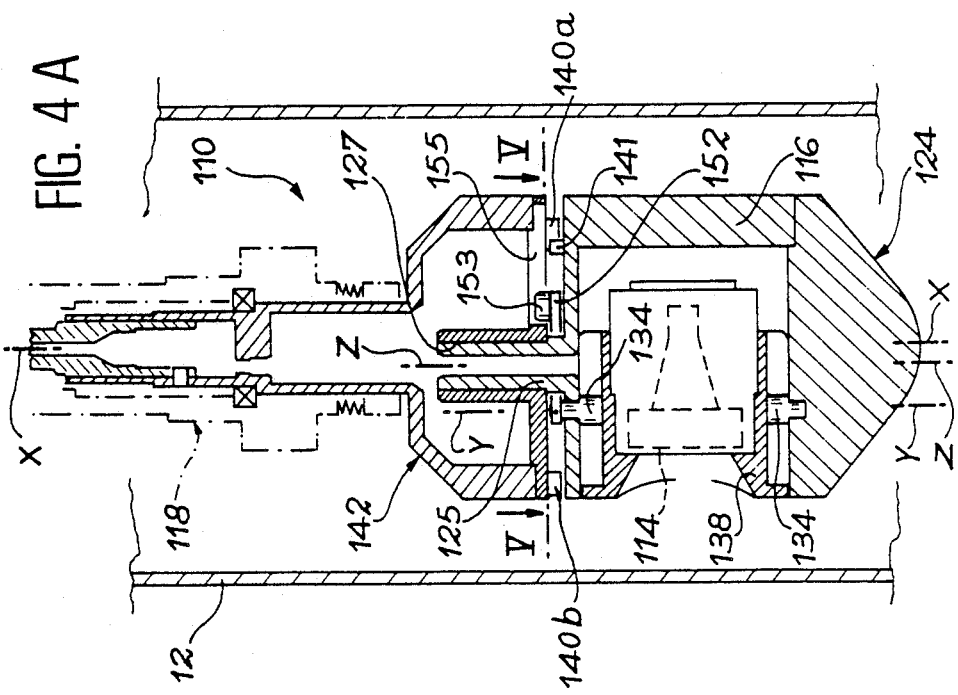

Measurement equipment 110 shown in FIG. 4A comprises sensor 114 interchangeably mounted on sensor support 138 hinged via two aligned pivots 134 about axis YY to target support 124. Target 116 is fixed on target support 124 in such a manner that rotation of sensor 114 through about 180° about axis YY makes it possible to bring the sensor face to face with the target. The top face of target support 124 includes hollow cylindrical rod 125 which is received in bore 127 formed in rotary head 142 which is itself rotatable inside outer tubular housing 118 of the equipment. More precisely, axis ZZ of bore 127 in which rod 125 is received lies parallel to and is offset from longitudinal axis XX of measurement head 110, which axis XX constitutes the axis of rotation of head 142.

In order to allow sensor 114 to be driven in rotation when rotary head 142 rotates about axis XX, U-shaped link 152 (more clearly visible in FIGS. 5A to 5C) is keyed at one of its ends to the end of top pivot 134, and carries stud 153 at its opposite end, which stud is received in radial slot 155 formed in the bottom face of rotary head 142. This link 152 which is disposed in a radial plane relative to longitudinal axis XX between rotary head 142 and target support 124 thus serves to transmit any rotary motion in either direction of rotary head 142 to sensor 114.

In addition, the axis of radial slot 155 intersects axes XX and ZZ and this groove is situated on the opposite side of axis XX to axis ZZ. In addition, the observation axis of sensor 114 lies in a radial plane relative to axis YY in which the axis of stud 153 is situated such that when the sensor is oriented radially towards the wall of the borehole in which the equipment is placed, axis of rotation ZZ of target support 124 lies between longitudinal axis XX of the equipment and axis of rotation YY of the sensor (see FIGS. 4A and 5A). This position, which is the measurement position, is normally maintained during clockwise rotation of head 142 as shown in FIG. 5A by abutment 140a fixed on the bottom face of the head coming into abutment against complementary abutment 141 fixed on the top face of the target support (in FIGS. 5A to 5C, the outlines of rotary head 142 and of target support 124 are drawn, respectively, by means of a dot-dashed line and a solid line, respectively).

During clockwise rotation of head 142 under the control of appropriate means (not shown) situated in the top portion of the equipment, the assembly comprising target support 124, target 116, sensor support 138, and sensor 114 rotates in unison about longitudinal axis XX of the equipment. This rotation allows sensor 114 to perform the desired measurements.

In accordance with the invention, when it is desired to bring the sensor face to face with the target, e.g. for calibrating the sensor within the borehole, then it suffices to reverse the direction of rotation of head 142. As shown successively in FIGS. 5B and 5C, the rotation of head 142 is then transmitted only to sensor 114 via link 152. Under the effect of inertia and friction, target support 124 tends to stop moving such that throughout this stage its orientation is assumed to remain unaltered in FIGS. 5A and 5C.

Figure 5C:
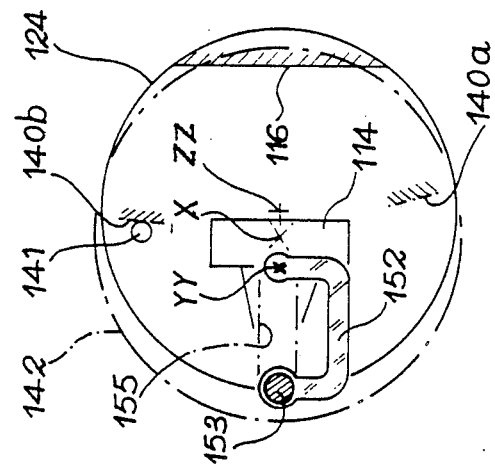
FIGS. 5A to 5C are diagrammatic section views on line V—V of FIG. 4A respectively showing three relative positions of the sensor, the target support, and the rotary head of the equipment.
Figure 5B:
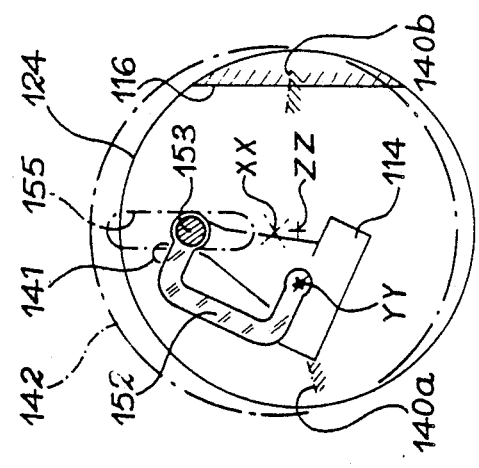
Figure 5A:
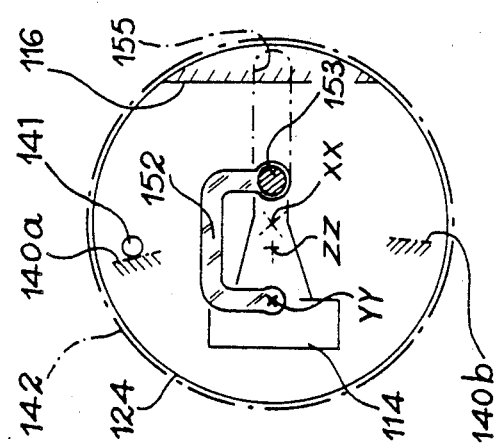

When the assembly constituted by rotary head 142 and sensor 114 has thus rotated through about 180 degrees, about axes XX and YY respectively, axis ZZ about which target support 124 rotates relative to head 142 again lies in the same plane as axes XX and YY, but this time axis XX lies between axes YY and ZZ (as shown in FIG. 5C). As can be seen in FIGS. 4B and 4C, sensor 114 then faces target 116 and the assembly constituted by these two items is automatically recentered relative to axis XX of the equipment, such that target 116 projects from one side and sensor 114 projects from the opposite side of head 142, by approximately the same amount. The sensor and the target are kept in this relative position during which the sensor can be calibrated by abutment 141 fixed on the top face of target support 124 coming into abutment against second abutment 140b placed on the bottom face of rotary head 142, as can be seen in FIG. 5C.

As in the first described embodiment, the distance then existing between sensor 114 and target 116 is designed to be approximately equal to the distance which exists during measurement between the sensor and the wall of the borehole.

Advantageously, measuring equipment 110 shown in FIGS. 4A and 4B includes, as before, an interchangeable bottom portion enabling the equipment to be adapted to boreholes of different diameters. Similarly, sensor 114 is mounted on support 138 in removable manner in order to enable it to be replaced.

Sensor 114 is fed with electricity and the signals it delivers are transmitted by electrical conductors (not shown) passing through rotary head 142, then inside hollow cylindrical rod 125, and connected to the sensor via support 138.

Finally, sealing means comparable to those used in the first embodiment are likewise provided.

Naturally, the invention is not limited to the embodiments described above by way of example, but it extends to any variant thereof.

Thus, in the embodiment shown in FIGS. 4 and 5, rotary head 142 could be freely mounted inside casing 116 of the equipment and sensor 114 could be rotated directly on target support rod 125 via a mechanism actuated by a rotary shaft placed inside head 142. This mechanism may be a link mechanism as in the first embodiment. These mechanisms may also be replaced by any equivalent mechanism, e.g., of the universal joint type.

In addition, it will readily be understood that the angle through which reverse rotation can take place in order to bring the face to face with the target need not to be 180°, the only condition that needs to be satisfied being that the angle should be sufficient to ensure that the target is hidden from the sensor while the sensor is rotating in the measurement direction.

Finally, the means for transmitting the rotary motion of the sensor to the target together with limited angular lost motion may be replaced by any other means for controlling relative displacement between the target and the sensor when the direction of rotation is reversed.

Although illustrative embodiments of the present invention have been described in detail with reference to the accompanying drawings, it is to be understood that the invention is not limited to those precise embodiments. Various changes or modifications may be effected therein by one skilled in the art without departing from the scope or spirit of the invention.

What I claim as my invention is:

1. A method of calibrating measurements in situ obtained by logging a portion of a casing cemented to a formation traversed by a borehole, said method employing a sonde having a sensor rotatable to circumferentially sense the cemented casing and rotatable to sense a calibration target, the calibration target having characteristics substantially similar to characteristics of the casing, said method comprising the steps of:
   directing the sensor to sense a first portion of the cemented casing;
   circumferentially sensing the first portion of the cemented casing;
   rotating the sensor in situ to sense the calibration target, thereby obtaining a reference measurement for calibrating the sensor;
   rotating the sensor to sense a second portion of the cemented casing; and
   circumferentially sensing the second portion of the cemented casing.

2. The apparatus according to claim 1, wherein the distance between the face of the sensor and the calibration target when the sensor is facing the calibration target is substantially equal to the distance between the face of the sensor and the cemented casing when the sensor is facing the cemented casing.

3. The method according to claim 1, wherein the sensor is rotated about an axis substantially parallel to the longitudinal axis of the borehole, and the sensor and the target are brought face to face substantially perpendicularly to said longitudinal axis.

4. The method according to claim 3, wherein the calibration target has limited angular lost motion relative to the sensor.

5. A logging sonde for logging a portion of a casing cemented to a formation traversed by a borehole and for calibrating these logging measurements in situ obtained thereby, said sonde comprising:
  a calibration target having characteristics substantially similar to characteristics of the casing;
  a sensor rotatable to circumferentially sense the cemented casing and rotatable to sense said calibration target;
  drive means for rotating said sensor about an axis, thereby enabling said sensor to scan either the cemented casing or said calibration target.

6. The apparatus according to claim 5, wherein said drive means comprises motion transmission means defining limited angular lost motion.

7. The apparatus according to claim 6, wherein said limited angular lost motion corresponds to rotation through about 180°.

* * * * *